US009789264B2

(12) United States Patent
Roberts et al.

(10) Patent No.: US 9,789,264 B2
(45) Date of Patent: Oct. 17, 2017

(54) INJECTION DEVICE WITH NEEDLE SHIELD

(71) Applicant: SANOFI-AVENTIS DEUTSCHLAND GMBH, Frankfurt am Main (DE)

(72) Inventors: Gareth Roberts, Wrexham (GB); Chris Ward, Denbighshire (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 520 days.

(21) Appl. No.: 14/538,331

(22) Filed: Nov. 11, 2014

(65) Prior Publication Data
US 2015/0065962 A1 Mar. 5, 2015

Related U.S. Application Data

(63) Continuation of application No. 13/807,044, filed as application No. PCT/EP2011/060321 on Jun. 21, 2011, now Pat. No. 8,911,401.

(30) Foreign Application Priority Data

Jul. 2, 2010 (EP) .................................. 10168321

(51) Int. Cl.
A61M 5/31 (2006.01)
A61M 5/32 (2006.01)
A61M 5/28 (2006.01)

(52) U.S. Cl.
CPC ........ *A61M 5/3272* (2013.01); *A61M 5/3202* (2013.01); *A61M 5/326* (2013.01);
(Continued)

(58) Field of Classification Search
CPC .......... A61M 5/326; A61M 2005/3247; A61M 2005/3267; A61M 5/2033; A61M 5/321;
(Continued)

(56) References Cited

U.S. PATENT DOCUMENTS 4,232,669 A * 11/1980 Nitshke ............... A61M 5/3202
604/192
4,871,355 A 10/1989 Kikkawa
(Continued)

FOREIGN PATENT DOCUMENTS

EP 1334740 8/2003
FR 2884722 10/2006
(Continued)

OTHER PUBLICATIONS

International Search Report for Int. App. No. PCT/EP2011/060321, completed Sep. 16, 2011.
(Continued)

Primary Examiner — Scott Medway
(74) Attorney, Agent, or Firm — Fish & Richardson P.C.

(57) ABSTRACT

According to the invention, an injection device (D) comprises a pre-filled syringe and a safety device. The pre-filled syringe comprises a barrel with an inner cavity in fluid communication with a hypodermic needle attached to a distal end of the pre-filled syringe and a piston fluid-tightly sealing a proximal end of the inner cavity. The safety device comprises a support body for retaining the pre-filled syringe therein, an outer body operably connected to the piston, a needle shield and a releasable retaining means (R). The retaining means comprises a radial projection and a longitudinal recess adapted to receive the radial projection. The radial projection is connected to or integral part of one of the support body or the outer body and a longitudinal recess formed into the other of the support body or the outer body. The needle shield, the support body and the outer body are telescopable relative to each other. The piston is movable in a distal direction to expel a medicament contained in the inner cavity through the hypodermic needle by a manual actuation of the outer body. A telescoping movement of the outer body with respect to the support body is restricted by (Continued)

the retaining means (R) when the needle shield is moved with respect to the support body in a proximal direction from an initial position (I) towards a retracted position (II). The retaining means (R) is released when the needle shield reaches the retracted position (II) allowing for a telescoping movement of the outer body with respect to the support body to expel the medicament contained in the pre-filled syringe through the hypodermic needle.

11 Claims, 9 Drawing Sheets

(52) U.S. Cl.
 CPC ............ *A61M 5/3287* (2013.01); *A61M 5/28* (2013.01); *A61M 5/3204* (2013.01); *A61M 2005/3267* (2013.01)

(58) Field of Classification Search
 CPC .... A61M 2005/206; A61M 2005/2073; A61M 2005/3268; A61M 25/0631; A61M 5/3257
 See application file for complete search history.

(56) References Cited

U.S. PATENT DOCUMENTS

| | | | |
|---|---|---|---|
| 4,923,447 A | 5/1990 | Morgan | |
| 5,279,579 A | 1/1994 | D'Amico | |
| 5,300,039 A * | 4/1994 | Poulsen | A61M 5/3243 604/198 |
| 5,312,366 A * | 5/1994 | Vailancourt | A61M 5/326 604/192 |
| 5,498,244 A | 3/1996 | Eck | |
| 5,527,294 A * | 6/1996 | Weatherford | A61M 5/3271 604/110 |
| 5,599,309 A | 2/1997 | Marshall et al. | |
| 5,746,215 A * | 5/1998 | Manjarrez | A61M 25/0637 600/573 |
| 7,201,740 B2 * | 4/2007 | Crawford | A61M 25/0631 604/110 |
| 8,172,810 B2 * | 5/2012 | Liversidge | A61M 5/326 604/192 |
| 8,512,295 B2 * | 8/2013 | Evans | A61M 5/3202 215/216 |
| 8,597,255 B2 * | 12/2013 | Emmott | A61M 5/002 604/110 |
| 2002/0087180 A1 * | 7/2002 | Searle | A61B 5/15142 606/181 |
| 2003/0144632 A1 * | 7/2003 | Hommann | A61M 5/326 604/198 |
| 2006/0167411 A1 * | 7/2006 | Weston | A61M 5/326 604/110 |
| 2007/0111175 A1 * | 5/2007 | Raven | G09B 23/285 434/262 |
| 2008/0167611 A1 | 7/2008 | Miller | |
| 2013/0190693 A1 * | 7/2013 | Ekman | A61M 5/2033 604/192 |
| 2013/0204195 A1 * | 8/2013 | Ekman | A61M 5/2033 604/197 |

FOREIGN PATENT DOCUMENTS

| | | |
|---|---|---|
| FR | 2884723 | 10/2006 |
| WO | 2007/047200 | 4/2007 |
| WO | 2008/025179 | 3/2008 |

OTHER PUBLICATIONS

International Preliminary Report on Patentability for Int. App. No. PCT/EP2011/060321, mailed Oct. 11, 2012.

\* cited by examiner

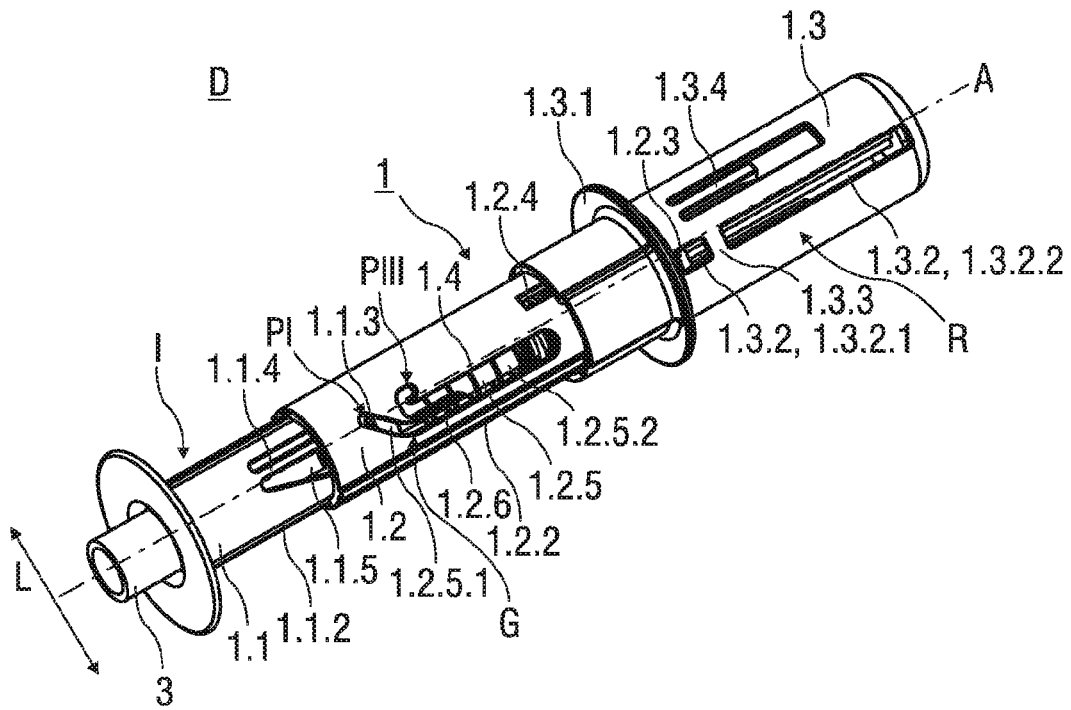

INJECTION DEVICE WITH NEEDLE SHIELD

CROSS REFERENCE TO RELATED APPLICATIONS

The present application is a continuation of U.S. patent application Ser. No. 13/807,044, filed Apr. 29, 2013, which is a U.S. National Phase Application pursuant to 35 U.S.C. §371 of International Application No. PCT/EP2011/060321 filed Jun. 21, 2011, which claims priority to 10168321.7 Patent Application No. Jul. 2, 2010 filed on Jul. 2, 2010. The entire disclosure contents of these applications are herewith incorporated by reference into the present application.

FIELD OF INVENTION

The present invention relates to an injection device comprising a pre-filled syringe and a safety device that provides needle safety for a hypodermic needle of the pre-filled syringe. The safety device is adapted to avoid accidental needle stick injuries before, during and after an injection of a medicament or drug contained in the pre-filled syringe. The injection device is easy and safe to use and is well suited for a self-administrated injection or for an injection administered by a health-care professional.

BACKGROUND

Pre-filled syringes that are filled with a selected dosage of a medicament are well known devices for administering the medicament to a patient. Safety devices for covering a needle of a pre-filled syringe before and after use are also well known. Typically, a needle shield of the safety device is either manually moved or moved by the action of a relaxing spring to surround the needle.

A different type of safety devices known in the state of the art solve the object of providing needle safety by arranging the pre-filled syringe movable relative to a body, wherein the pre-filled syringe is retracted into the body after the injection.

Amongst others, injection devices known in the state of arts comprise a safety device and a pre-filled syringe that is retained within the safety device, so that an injection can be safely performed.

Document FR 2 884 722 discloses an injection device comprising a syringe, an outer body, a spring-loaded inner sleeve, an outer and an inner needle shield. The spring-loaded inner sleeve is connected to a plunger of the syringe so that a medicament contained in the syringe may be expelled upon release of the spring. Initially, the inner sleeve is retained against the biasing force of the spring in by retaining means and the outer needle shield surrounds an injection needle. The retaining means are released upon translation of the outer needle shield into a proximal position uncovering the injection needle. The released inner sleeve urges the plunger in the distal direction to expel the medicament through the injection needle. After the drug is delivered, the spring further urges the inner needle shield distally to cover the injection needle to provide needle safety.

FR 2 884 722 A1 discloses an injection support device for an injection device comprising at least one body. at least one needle and at least one piston seal housed in said body. further comprising at least:
a sheath provided with at least one support surface.
a sleeve movable relative to said sleeve and having at least one gripping area. said sleeve having coupling means for linking said gripping area to said piston seal or to said body for axial translation from an initial position to an insertion position.

WO 2007/047200 A1 discloses a pharmaceutical delivery apparatus including a housing. a syringe assembly. and a needle cap. The syringe assembly is plungeable relative to the housing from a first position. at which its needle tip is disposed within the housing. to a second position. at which its needle tip projects from the housing beyond the proximal end for insertion into an injection site. A base of the needle cap is exposed at the housing proximal end to be manually grippable for cap removal. A needle cap stem is upstanding from the base and sized and configured to insert through an opening is the housing proximal end to cover the needle tip when the syringe assembly is disposed in the first position. The needle cap base further includes a plurality of distally projecting cams located radially outward of the stem. The cams are fittable within slots in the housing proximal end when the cap is fully mounted to the apparatus.

SUMMARY

It is an object of the present invention to provide an improved injection device comprising a safety device and a pre-filled syringe.

The object is achieved by an injection device according to claim 1.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, an injection device comprises a pre-filled syringe and a safety device. The pre-filled syringe comprises a barrel with an inner cavity in fluid communication with a hypodermic needle attached to a distal end of the pre-filled syringe and a piston fluid-tightly sealing a proximal end of the inner cavity. The safety device comprises a support body for retaining the pre-filled syringe therein, an outer body operably connected to the piston, a needle shield and a releasable retaining means. The retaining means comprises a radial projection and a longitudinal recess adapted to receive the radial projection. The radial projection is connected to or integral part of one of the support body or the outer body and a longitudinal recess formed into the other of the support body or the outer body. The needle shield, the support body and the outer body are telescopable relative to each other. The piston is movable in a distal direction to expel a medicament contained in the inner cavity through the hypodermic needle by a manual actuation of the outer body. A telescoping movement of the outer body with respect to the support body is restricted by the retaining means when the needle shield is moved with respect to the support body in a proximal direction from an initial position towards a retracted position. The retaining means is released when the needle shield reaches the retracted position allowing for a telescoping movement of the outer body with respect to the support body to expel the medicament contained in the pre-filled syringe through the hypodermic needle.

The injection device allows a stage-wise movement of the needle shield, the support body and the outer body during the injection. In the first stage of the injection, the needle shield moves from the initial position to the retracted position. The hypodermic needle penetrates the skin of the patient when the needle shield reaches the retracted position. In the second stage of the injection, the outer body is moved relative to the support body to expel a medicament contained in the pre-filled syringe through the hypodermic needle. The retaining means restricting the telescoping movement of the outer body with respect to the support body thus ensure that the medicament is expelled after the hypodermic needle penetrated the skin surface of the patient. In particular, a spilling of the medicament before the injection is avoided.

A guiding means retains the needle shield with respect to the support body in various positions and guides the telescoping movement of the needle shield with respect to the support body between those various positions. In particular, the guiding means guide the movement of the needle shield from the initial position to the retracted position. Frictional forces between the needle shield, the support body and the guiding means are adapted to be lower than a retention force of the retaining means that restricts the telescoping movement of the outer body with respect to the support body. Therefore, the frictional forces are adapted to allow for a releasable retention of the outer body with respect to the support body by the retaining means until the needle shield reaches the retracted position.

According to a possible embodiment of the invention, the pre-filled syringe comprises a barrel with an inner cavity in fluid communication with the hypodermic needle attached to a distal end of the pre-filled syringe and a piston fluid-tightly sealing a proximal end of the inner cavity. The piston is movable in the distal direction to expel the medicament contained in the inner cavity through the hypodermic needle by a manual actuation of the outer body. The injection device is designed in a way that both the insertion of the hypodermic needle and the injection of the medicament are carried out by a user manually pushing the outer body in a single linear stroke in the distal direction. The stage-wise movement of the needle shield, the support body and the outer body relative to each other are ensured by the guiding means and the retaining means. Complicated mechanical mechanisms that in particular drive the piston to expel the medicament are avoided. The injection device comprises a low number of parts and is designed as a one-way device that is disposed after a single injection has been performed.

According to another possible embodiment of the invention, a piston rod is connected to the piston. The piston rod abuts the outer body, so that the piston can be pushed in the distal direction to expel the medicament by actuating the outer body. Alternatively, the piston rod is arranged with the outer body as one piece. The simple mechanism for moving the piston to expel the medicament provides a reliable use of the injection device.

According to yet another possible embodiment of the invention, the retaining means comprise a radial projection connected to or integral part of one of the support body or the outer body and a longitudinal recess formed into the other of the support body or the outer body. Thus, the support body may comprise a radial projection protruding in a radial outward direction and the longitudinal recess may be formed into the outer body. Alternatively, the outer body may comprise a radial projection protruding in a radial inward direction and the longitudinal recess may be formed into the support body. The longitudinal recess may have the form of a slot or may be formed into an inner surface of the outer body, or alternatively into the outer surface of the support body. The radial projection engages the longitudinal recess to retain the outer body with respect to the support body in a translational and rotational pre-defined position. In particular, a rotational movement of the outer body with respect to the support body is prevented by the engagement of the radial projection with the longitudinal recess.

According to yet another embodiment, the longitudinal recess comprises a first section and a second section separated by a web from each other. The web, the first and the second section of the longitudinal recess are integral to the outer body that is preferably made from a plastics material. The low number of parts allows for a cost-efficient mass-production of the injection device.

The radial projection engages the first section of the longitudinal recess to restrict the telescoping movement of the outer body with respect to the support body. The retention force required to deflect the radial projection, so that the radial projection may pass the web and may leave the first section of the longitudinal recess, is adapted to the force required to move the needle shield with respect to the support body from the initial position to the retracted position. The retention force exceeds this required force, so that an early release of the retaining means is prevented until the needle shield reaches the retracted position.

The second section of the longitudinal recess extends over a substantial axial length of one of the outer body or the support body. The axial extension of the longitudinal recess prevents a rotation of the outer body relative to the support body throughout an entire injection stroke performed by a user to expel the medicament contained in the pre-filled syringe.

When the needle shield reaches the retracted position, the needle shield abuts the support body. A force exerted by the user who pushes the outer body in the distal direction towards the skin surface of the patient exceeds the retention force retaining the outer body fixed relative to the support body. The radial projection is radial deflected and passes the web to release the retaining means. The radial projection engages the second section of the longitudinal recess when the retaining means are released, whereby the outer body is allowed to move with respect to the support body. The radial projection moves along the second section of the longitudinal recess when the outer body is moved with respect to the inner body to expel the medicament.

According to a possible embodiment, the guiding means comprise a guide pin connected to one of the needle shield or the support body and a guide track formed into the other of the needle shield or the support body. The guide pin may thus be connected to the needle shield and the guide track may be formed into the support body, or alternatively, the guide pin may be connected to the support body and the guide track may be formed to the needle shield. The guide pin protrudes into the guide track and moves along the guide track between various positions when the needle shield is moved relative to the support body. The guide pin interacts with the guide track in a way that prevents a multiple exposure of the hypodermic needle, so that a re-usage of the injection device is prevented after a first use.

According to another possible embodiment of the invention, the needle shield is releasably retained in the initial position by the guide pin being retained in a start position within the guide track. The hypodermic needle is surrounded by the needle shield in the initial position.

According to a possible embodiment, the needle shield is made from an opaque plastics material. The hypodermic needle is hidden from the view of the patient before the injection by the needle shield that is retained in the initial position. This eases a possible patient's fear of needles. The safety device is thus particularly suited for performing self-administered injections.

According to an alternative embodiment, the needle shield is made from a transparent plastics material. A healthcare professional that uses the safety device thus can visually confirm the correct placement of the hypodermic needle penetrating the skin of the patient, even when the hypodermic needle is surrounded by the needle shield.

As the safety device is both suited for self-administered injections and injections carried out by a healthcare professional, the person referred to as the user or the patient may be one and the same person.

According to yet another possible embodiment of the invention, the needle shield is movable in the distal direction from the retracted position to an advanced position, wherein the needle shield in the advanced position surrounds the hypodermic needle after an injection, so that inadvertent needle stick injuries with contaminated hypodermic needles are prevented.

According to yet another possible embodiment, the needle shield is permanently retained in the advanced position by the guide pin being retained in an end position defined by a U-shaped indent of the guide track. The needle shield is permanently locked to the advanced position surrounding the hypodermic needle after the first use of the injection device. The interaction of the U-shaped indent of the guide track and the guide pin provides an efficient means to lock the needle shield and to prevent a re-usage of the injection device, so that a risk of an infection is minimized.

Details of the present invention are described hereinafter. However, it should be understood that the detailed description and the specific examples indicate possible embodiments of the invention and are given by way of illustration only. Various changes and modifications of the illustrated embodiments within the spirit and scope of the invention are appreciated by those skilled in the art.

BRIEF DESCRIPTION

The present invention will be better understood from the detailed description given in the following. The accompanying drawings are given for illustrative purposes only and do not limit the scope of the present invention.

FIG. 1 shows a perspective view of an injection device according to a first embodiment prior to use, wherein the injection device comprises a safety device and a pre-filled syringe.

FIG. 2 shows a sectional view of the injection device according to the first embodiment with a needle shield retained in an initial position.

Corresponding parts are marked with the same reference symbols in all figures.

DETAILED DESCRIPTION

Figure 3:
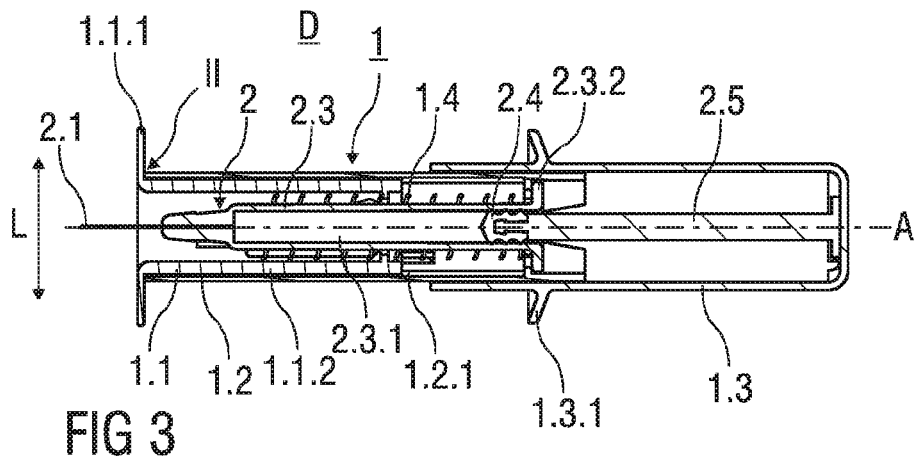
FIG. 3 shows a sectional view of the injection device according to the first embodiment with the needle shield retained in a retracted position.

FIG. 1 shows an injection device D according to a first embodiment of the invention in a packaged state as it would be presented to a user. The injection device D comprises a safety device 1 and a pre-filled syringe 2. The safety device 1 comprises a substantially cylindrical and hollow needle shield 1.1. The needle shield 1.1 is received within a substantially cylindrical and hollow support body 1.2. The needle shield 1.1 is slidable with respect to the support body 1.2. Before use of the safety device 1, the needle shield 1.1 is retained in an initial position I, wherein the needle shield 1.1 protrudes the support body 1.2 and surrounds a hypodermic needle 2.1 of the pre-filled syringe 2.

Alternatively, the needle shield 1.1 comprises a radial diameter that is sized to substantially receive the support body 1.2. In this alternative embodiment the support body 1.2 slides into the needle shield 1.1 when the needle shield 1.1 is moved from the initial position I to a refracted position II.

FIG. 1 shows an essentially cylindrical and hollow outer body 1.3 with an open distal and a closed proximal end. The proximal end of the support body 1.2 is received within the open distal end of the outer body 1.3 and the outer body 1.3 is movable in a telescoping motion with respect to the support body 1.2 in a distal direction to substantially receive the support body 1.2 inside the outer body 1.3.

A circumferential and outwardly protruding hand flange 1.3.1 is integrally formed to an exterior surface of the outer body 1.3 close to its distal end.

The needle shield 1.1, the support body 1.2 and the outer body 1.3 are telescopable relative to each other. Preferably, the needle shield 1.1, the support body 1.2 and the outer body 1.3 are made from a plastics material.

The needle shield 1.1 comprises a circumferential skin-contact flange 1.1.1 at its distal end. The skin-contact flange 1.1.1 is adapted to be pressed against the skin of a patient and protrudes radial outwardly and perpendicular to a central axis A of the safety device 1. Edges of the skin-contact flange 1.1.1 that come into contact with the skin of the patient are rounded to avoid injuries. The skin-contact flange 1.1.1 has a central opening centred on the central axis A of the safety device 1. The skin-contact flange 1.1.1 is integral to the needle shield 1.1, or alternatively, a separate part attached to the needle shield 1.1 that is made from a plastics material.

Two first longitudinal tongues 1.1.2 are formed to opposite sides of the needle shield 1.1. Each first longitudinal tongue 1.1.2 protrudes radial outwardly and extends over an axial length parallel to a central axis A of the needle shield 1.1. As best seen in FIG. 2, the first longitudinal tongue 1.1.2 is received in a corresponding first longitudinal groove 1.2.1 formed into an interior surface of the support body 1.2. A relative rotation of the support body 1.2 and the needle shield body 1.1 is prevented by the first longitudinal groove 1.2.1 receiving the first longitudinal tongue 1.1.2 of the needle shield 1.1.

As illustrated in FIG. 1, the support body 1.2 comprises at least one second longitudinal tongue 1.2.2 that is received in a second longitudinal groove (not illustrated) formed into an inner surface of the outer body 1.3, whereby a relative rotation of outer body 1.3 and support body 1.2 is prevented.

A retaining means R of the safety device 1 comprises at least one longitudinal recess 1.3.2 and at least one radial projection 1.2.3. The longitudinal recess 1.3.2 is sized to receive the radial projection 1.2.3.

In the first embodiment shown in FIG. 1, two longitudinal recesses 1.3.2 are formed into the opposite sides of the outer body 1.3. The longitudinal recess 1.3.2 comprises two sections, a first section 1.3.2.1 and a second section 1.3.2.2 separated by a web 1.3.3 from each other. The second section 1.3.2.2 of the longitudinal recess 1.3.2 extends over a substantial axial length of the outer body 1.3 and parallel to the central axis A.

Each longitudinal recess 1.3.2 receives a corresponding radial projection 1.2.3 integral to the support body 1.2. The radial projection 1.2.3 moves within the longitudinal recess 1.3.2 when the outer body 1.3 is moved relative to the support body 1.2 to perform the injection stroke, whereby a rotation of the outer body 1.3 relative to the support body 1.2 is prevented.

Prior the injection, the radial projection 1.2.3 is retained in the first section 1.3.2.1 of the longitudinal recess 1.3.2. The radial projection 1.2.3 is deflectable in a radial inward direction, so that the radial projection 1.2.3 may leave the first section 1.3.2.1 and enter the second section 1.3.2.2 when the outer body 1.3 is pushed with respect to the support body 1.2 in the distal direction. The shape and elasticity of the radial projection 1.2.3 and the first section 1.3.2.1 of the longitudinal recess 1.3.2 are adjusted in a manner that a force required for the radial projection 1.2.3 to leave the first section 1.3.2.1 exceeds a force required to move the needle shield 1.1 from the initial position I to the retracted position II. This ensures a stage-wise movement of the needle shield 1.1, the support body 1.2 and the outer body 1.3 during the injection as described in more detail herein below.

Alternatively, the radial projection 1.2.3 is connected to the outer body 1.3 and protrudes in a radial inward direction. In this alternative embodiment, the longitudinal recess 1.3.2 sized to receive the radial projection 1.2.3 is formed into the support body 1.2.

The longitudinal recess 1.3.2 shown in FIG. 1 has the form of a slot. Alternatively, the longitudinal recess 1.3.2 is formed into an inner surface of the outer body 1.3, so that the radial projection 1.2.3 moves along the longitudinal recess 1.3.2 within the outer body 1.3 and is inaccessible from the outside.

Figure 5:
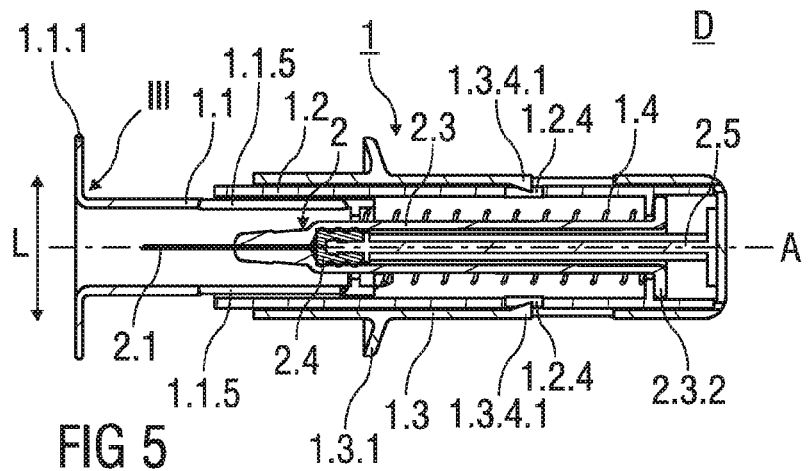
FIG. 5 shows a sectional view of the injection device according to the first embodiment after an injection has been performed.

A clamp arm 1.3.4 is formed into the substantially cylindrical outer body 1.3 that is deflectable in the radial direction perpendicular to the central axis A. As best seen in FIG. 5, the clamp arm 1.3.4 comprises an inwardly protruding locking catch 1.3.4.1 that is sized to fit into a locking recess 1.2.4 formed into the support body 1.2 in proximity of a proximal end of the support body 1.2.

FIG. 1 shows a guiding means G of the safety device 1. The guiding means G comprises at least one guide pin 1.1.3 and at least one guide track 1.2.5 that accommodates that guide pin 1.1.3. The guide pin 1.1.3 is moved along the guide track 1.2.5 between various positions to retain the needle shield 1.1 in various positions relative to the support body 1.2. Additionally, the interaction of the guide pin 1.1.3 with the guide track 1.2.5 guides the movement of the needle shield 1.1 and in particular allows only for a single retraction of the needle shield 1.1 towards the retracted position II during the first use of the injection device D.

In the first embodiment illustrated in FIG. 1, two guide tracks 1.2.5 are formed into opposite sides of the support body 1.2. Each guide track 1.2.5 accommodates a guide pin 1.1.3 that is integrally formed to a flexible arm 1.1.4 of the needle shield 1.1. The flexible arm 1.1.4 extends in its rest position essentially parallel to the central axis A of the safety device 1. As illustrated in FIG. 1, the guide pin 1.1.3 protrudes radial outwardly into a guide track 1.2.5 formed into the substantially cylindrical support body 1.2. A trapezoid cut-out 1.1.5 is formed into the needle shield 1.1 adjacent to the flexible arm 1.1.4 to allow for a deflection and pivoting movement of the flexible arm 1.1.4. Prior to use of the safety device 1, the guide pin 1.1.3 is retained within an inclined section 1.2.5.1 of the guide track 1.2.5 in a start position PI located at a distal end of the guide track 1.2.5. As the flexible arm 1.1.4 is in the rest position, the guide pin 1.1.3 is laterally non-biased in the start position PI. The inclined section 1.2.5.1 is oriented at an acute angle relative to the central axis A of the safety device 1.

In an alternative embodiment, the guide track 1.2.5 is formed into the needle shield 1.1 and the guide pin 1.1.3 is connected to the support body 1.2.

The needle shield 1.1 is retained in an initial position I by the guide pin 1.1.3 being retained in a start position PI in the inclined section 1.2.5.1 of the guide track 1.2.5. The needle shield 1.1 is made from an opaque plastics material, so that the hypodermic needle 2.1 is hidden from view of the patient before the injection.

Alternatively, the needle shield 1.1 is made from a transparent plastics material, so that a healthcare professional performing the injection may visually confirm the correct placement of the hypodermic needle 2.1 before penetrating the skin of the patient.

The guide pin 1.1.3 is prevented from leaving the start position PI by an interaction of several components of the safety device 1: The flexible arm 1.1.4 biases the guide pin 1.1.3 in a lateral direction L perpendicular to the central axis A, the guide pin 1.1.3 abuts the distal end of the inclined section 1.2.5.1 in the lateral direction L and distal direction and a compression spring 1.4, as best seen in FIG. 2, is arranged between the support body 1.2 and the needle shield 1.1, so that the needle shield 1.1 and the guide pin 1.1.3 connected thereto is biased in the distal direction.

The guide track 1.2.5 comprises a widened section 1.2.5.2 extending parallel to the central axis A of the safety device 1. A flexible separating wall 1.2.6 extends parallel to the central axis A and into the widened section 1.2.5.2 from a distal direction. The flexible separating wall 1.2.6 is integral to the support body 1.2 and acts as a no-return feature preventing the guide pin 1.1.3 from returning to its start position PI after an injection stroke has been carried out. Furthermore, the flexible separating wall 1.2.6 guides the movement of the guide pin 1.1.3 within the guide track 1.2.5, so that the guide pin 1.1.3 is prevented to enter an end position PIII from the distal direction, whereas the guide pin 1.1.3 is allowed to enter the end position PIII from the proximal direction. The end position PIII is defined by a generally U-shaped indent between the distal and a proximal end of the guide track 1.2.5.

The injection device D comprises the safety device 1 with the pre-filled syringe 2 retained within the support body 1.2.

FIG. 2 shows the pre-filled syringe 2 received within the support body 1.2 that comprises a hypodermic needle 2.1 covered by a needle cap 2.2 frictionally affixed to a distal end of a barrel 2.3. The barrel 2.3 has an inner cavity 2.3.1 containing a medicament. The inner cavity 2.3.1 is in fluid communication with the hypodermic needle 2.1. A proximal end of the inner cavity 2.3.1 is fluid-tightly sealed by a piston 2.4 that is connected to piston rod 2.5. The piston 2.4 is movable in at least the distal direction by actuating the piston rod 2.5 protruding the barrel 2.3 in the proximal direction. The barrel 2.3 of the pre-filled syringe 2 comprises a barrel collar 2.3.2 that abuts a radial inwardly protruding inner surface of the support body 1.2 at its proximal end affixing the pre-filled syringe 2 to the support body 1.2.

Figure 4:
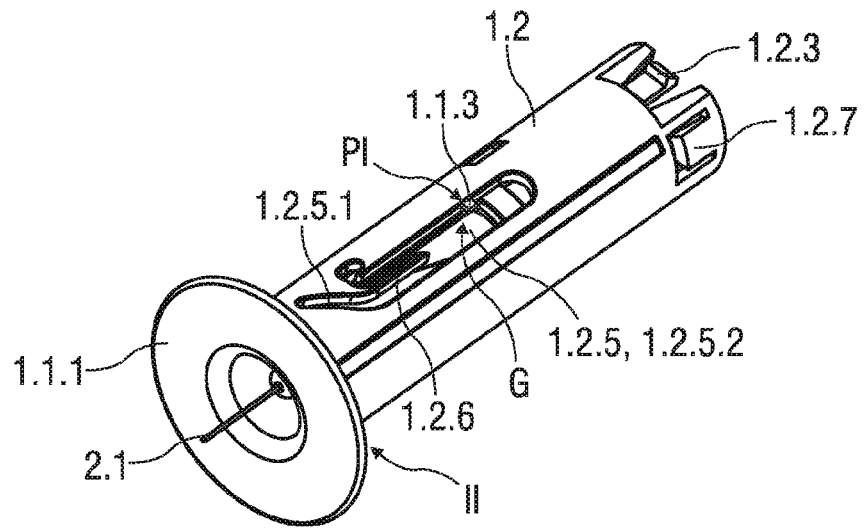
FIG. 4 shows a perspective view of a support body and the needle shield according to the first embodiment, wherein the needle shield is retained in a retracted position.

With cross-reference to FIG. 4, it can be seen that the support body 1.2 comprises clips 1.2.7 that engage the barrel collar 2.3.2 to retain the pre-filled syringe 2 within the support body 1.2.

As illustrated in FIG. 2, the pre-filled syringe 2 is retained within the support body 1.2, whereby the hypodermic needle 2.1 protrudes the support body 1.2 in the distal direction.

In the packaged state shown in FIGS. 1 and 2, the hypodermic needle 2.1 is covered by a needle cap 2.2 that is surrounded by the needle shield 1.1 prior to use of the injection device D. The needle cap 2.2 is preferably at least partially made from a plastics material like an elastomer or rubber. The width of a central opening of the skin contact flange 1.1.1 corresponds to an outer diameter of the needle cap 2.2. A needle cap remover 3 is inserted into the central opening of the skin-contact flange 1.1.1 and protrudes the skin-contact flange 1.1.1 in a distal direction, so that the user can easily remove the needle cap 2.2 from the pre-filled syringe 2 by pulling the needle cap remover 3 in the distal direction. The needle cap remover 3 comprises clamp means 3.1 that clamp to a distal end of the needle cap 2.2.

Alternatively, the injection device D comprising the safety device 1 with the pre-filled syringe 2 retained therein is shipped and delivered to an end-user with a needle cap remover 3 attached to the distal end of the needle cap 2.2, so that the needle cap remover 3 protrudes the needle shield 1.1 in the distal direction.

A proximal end of the piston rod 2.5 abuts the closed distal end of the outer body 1.3, so that the piston 2.4 is movable in a distal direction by the distal displacement of the outer body 1.3 with respect to the support body 1.2.

Alternatively, the piston rod 2.5 is connected to the outer body 1.3 or an integral part of the outer body 1.3. This alternative embodiment has additional advantage of a low overall part count, so that manufacturing costs are reduced.

The needle shield 1.1 is in the initial position I surrounding the hypodermic needle 2.1 of the pre-filled syringe 2. The compression spring 1.4 is arranged within the safety device 1 in a partially energized state bearing distally against an inner surface of the needle shield 1.1 and proximally against an inner surface of the support body 1.2, thereby biasing these two parts 1.1, 1.2 away from each other. The needle shield 1.1 is retained in the initial position I by the guide pin 1.1.3 abutting against the support body 1.2 in the start position PI.

FIG. 3 shows a sectional view of the needle shield 1.1 in the retracted position II, wherein the needle shield 1.1 is substantially received within the support body 1.2. The hypodermic needle 2.1 distally protrudes the skin-contact flange 1.1.1 of the needle shield 1.1. The compression spring 1.4 that is arranged within the safety device 1 is fully compressed and thus fully energized.

FIG. 4 shows a perspective view of the needle shield 1.1 in the retracted position II, wherein the needle shield 1.1 is substantially received within the support body 1.2. The guide pin 1.1.3, that is integral part of the needle shield 1.1 is in an intermediate position PII within the guide track 1.2.5 and in proximity of a proximal end thereof. The intermediate position PII corresponds to the retracted position II of the needle shield 1.1.

The support body 1.2 further comprises two clips 1.2.7 diametrical opposite to each other. The clips 1.2.7 are located near the proximal end of the support body 1.2 and clamp to the collar 2.3.2 of the pre-filled syringe 2 to affix the pre-filled syringe 2 to the support body 1.2, so that the pre-filled syringe 2 is firmly retained within the support body 1.2.

FIG. 5 shows a sectional view of the safety device 1 after the injection of the medicament. The sectional view given in FIG. 5 is rotated with respect to the sectional views shown in FIGS. 2 and 3 about an angle of 90 degrees around the central axis A. The needle shield 1.1 is in an advanced position III protruding distally from the support body 1.2, wherein the hypodermic needle 2.1 is surrounded by the needle shield 1.1 to avoid accidental needle stick injuries. The needle shield 1.1 is fixed to the advanced position III by the guide pin 1.1.3 being retained in the end position PIII.

The piston 2.4 is fully depressed inside the barrel 2.3 of the pre-filled syringe 2. The support body 1.2 is received within the outer body 1.3 and locked to it, so that a re-usage of the safety device 1 is prevented. The inwardly protruding locking catch 1.3.4.1 formed to the clamp arm 1.3.4 latches to the corresponding locking recess 1.2.4 formed into the support body 1.2 to irreversibly lock the support body 1.2 with respect to the outer body 1.3.

The injection is carried out by orientating the central axis A essentially perpendicular to the skin of the patient. The skin-contact flange 1.1.1 of the needle shield 1.1 rests on the skin surface of the patient and the proximal section of the outer body 1.3 proximal of the hand flange 1.3.1 is gripped by the user performing the injection. The hand flange 1.3.1 supports the hand of the user to carry out an injection stroke, whereby the outer body 1.3 is moved distally towards the skin surface of the patient.

FIGS. 6A to 6F show details of the guide track 1.2.5 formed into the support body 1.2 and the movement of the guide pin 1.1.3 within the guide track 1.2.5 during use of the safety device 1.

Figure 6A:
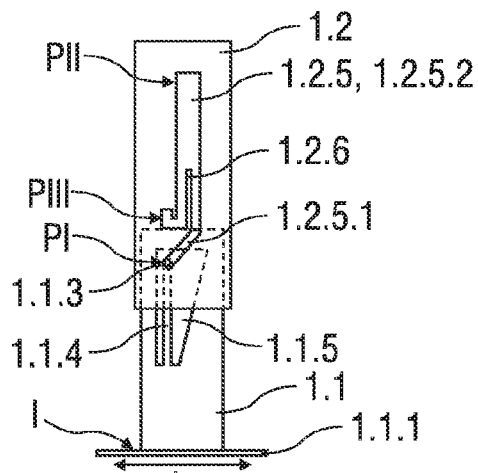
FIGS. 6A to 6F show details of a guide track and the movement of a guide pin within the guide track according to the first embodiment.

As shown in FIG. 6A, the guide pin 1.1.3 is retained prior to the injection in the start position PI at the distal end of the inclined section 1.2.5.1 of the guide track 1.2.5, affixing the needle shield 1.1 to the initial position I. In the initial position I, the hypodermic needle 2.1 is surrounded by the needle shield 1.1.

Figure 6B:
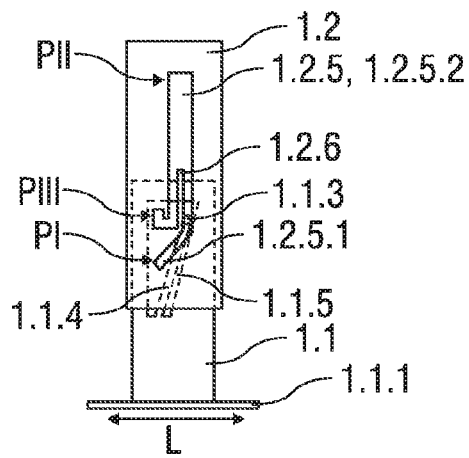

The injection is carried out in stages. In a first stage, the hypodermic needle 2.1 is inserted into the skin of the patient. The needle shield 1.1 is pushed inside the support body 1.2 in the proximal direction against the biasing force of the compression spring 1.4. As illustrated in FIGS. 6A and 6B, the guide pin 1.1.3 leaves its start position PI and moves along the inclined section 1.2.5.1 of the guide track 1.2.5. As the distal end section 1.2.5.1 is oriented at an acute angle relative to the central axis A, the movement of the guide pin 1.1.3 causes the flexible arm 1.1.4 to become laterally deflected and stressed, so that the guide pin 1.1.3 is biased in the lateral direction L.

Figure 6C:
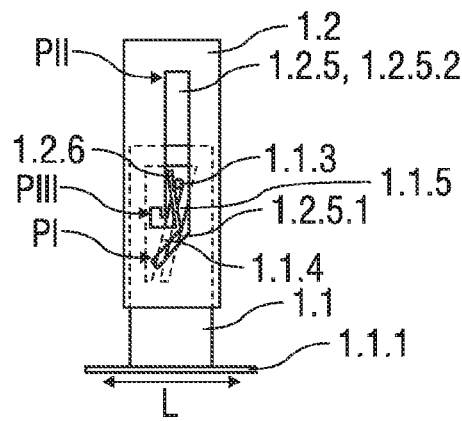

The guide pin 1.1.3 travels further along the guide track 1.2.5 in the proximal direction. As shown in FIG. 6C, the guide pin 1.1.3 enters the widened section 1.2.5.2 of the guide track 1.2.5 and abuts the flexible separating wall 1.2.6 in the lateral direction L. The flexible separating wall 1.2.6 is laterally deflected by a force exerted upon the flexible separating wall 1.2.6 by the stressed flexible arm 1.1.4. The elasticity of the flexible separating wall 1.2.6 is adapted to correspond to the elasticity of the flexible arm 1.1.4, so that the flexible separating wall 1.2.6 is deflectable by the deflected and stressed flexible arm 1.1.4.

The flexible separating wall 1.2.6 prevents the guide pin 1.1.3 from entering the end position PIII as the guide pin 1.1.3 enters the widened section 1.2.5.2 from the distal direction.

Figure 6D:
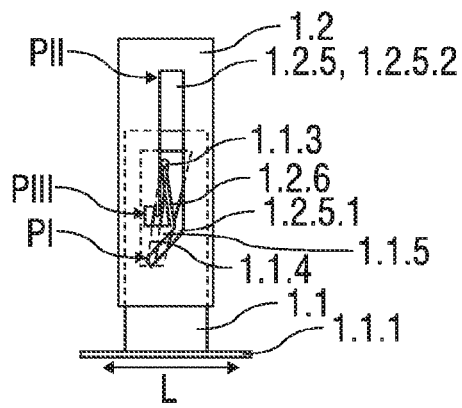

The guide pin 1.1.3 moves further proximally towards an intermediate position PII and reaches a proximal end of the flexible separating wall 1.2.6, as illustrated in FIG. 6D. At this point, the safety features of the safety device 1 are activated, as the flexible separating wall 1.2.6 relaxes and snaps back into its rest position substantially parallel to the central axis A. From now on, the end position PIII is accessible for the guide pin 1.1.3 to enter, whereas the guide pin 1.1.3 is prevented to re-enter the start position PI. A subsequent removal of the safety device 1 causes the needle shield 1.1 and the guide pin 1.1.3 to advance distally, so that the needle shield 1.1 surrounds the hypodermic needle 2.1 of the pre-filled syringe in the advanced position III. The needle shield 1.1 is firmly retained in the advanced position III by the guide pin 1.1.3 being retained in the U-shaped indent of the guide track 1.2.5 defining the end position PIII, whereby a re-usage of the injection and/or the safety device 1 is prevented.

The flexible separating wall 1.2.6 has an axial dimension extending parallel to the central axis A and into the widened section 1.2.5.2 of the guide track 1.2.5. The axial dimension defines a minimal axial distance the needle shield 1.1 has to be moved with respect to the support body 1.2 before the advanced position III is accessible for the needle shield 1.1 to enter and the safety features preventing the re-use of the safety device 1 are activated. This avoids an unintentional activation of the safety features of the safety device 1, when the needle shield 1.1 is accidentally pushed distally by an axial length that is smaller than the minimal axial distance.

The safety device 1 generates an audible feedback indicating the activation of the safety features. The audible feedback can be generated by the flexible separating wall 1.2.6 snapping back into its rest position substantially parallel to the central axis A when the needle shield 1.1 is moved distally with respect to the support body 1.2 by an axial length that exceeds the minimal axial distance.

In order to inject the medicament, the needle shield 1.1 is moved further in the proximal direction until it reaches the retracted position II illustrated in FIG. 3, whereby the guide pin 1.1.3 is retained within the guide track 1.2.5 in the intermediate position PII. The compression spring 1.4 is fully compressed and fully charged. The hypodermic needle 2.1 penetrates the skin of the patient, so that the medicament contained in the inner cavity 2.3.1 can be injected in the following second stage of the injection.

Throughout the first stage of the injection, the radial projection 1.2.3 is retained in the first section 1.3.2.1 of the longitudinal recess 1.3.2, whereby a distal movement of the outer body 1.3 with respect to the support body 1.2 is prevented. When the guide pin 1.1.3 reaches the intermediate position PII and the needle shield 1.1 enters the corresponding retracted position II, the radial projection 1.2.3 deflects in the radial inward direction, leaves the first section 1.3.2.1 and enters the second section 1.3.2.2 of the longitudinal recess 1.3.2, so that the outer body 1.3 is allowed to move relative to the support body 1.2 in the second stage of the injection.

In the second stage, the outer body 1.3 moves with respect to the support body 1.1 in the distal direction. Simultaneously, the piston rod 2.5 interacting with the outer body 1.3 is actuated to move the piston 2.4 in the distal direction, whereby the medicament contained in the inner cavity 2.3.1 is delivered through the hypodermic needle 2.1 and beneath the skin of the patient.

At the end of the injection stroke, the inwardly protruding locking catch 1.3.4.1 formed to the clamp arm 1.3.4 latches to the corresponding locking recess 1.2.6 formed into the support body 1.2 to irreversibly lock the support body 1.2 with respect to the outer body 1.3.

Figure 6E:
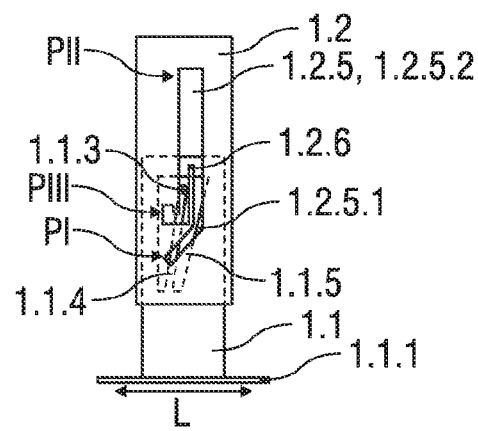

The injection device D comprising the safety device 1 with the pre-filled syringe 2 received therein is removed from the skin surface. The needle shield 1.1 immediately moves distally towards the advanced position III by the action of the relaxing compression spring 1.4. As indicated in FIG. 6E, the guide pin 1.1.3 jointly moves with the needle shield 1.1 distally, whereby the guide pin 1.1.3 is guided by the flexible separating wall 1.2.6 towards the end position PIII.

Figure 6F:
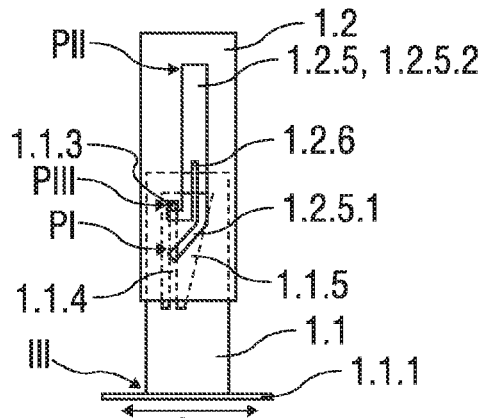

As indicated in FIG. 6F, the guide pin 1.1.3 enters the U-shaped indent defining the end position PIII of the guide track 1.2.5, whereby the flexible arm 1.1.4 relaxes to move the guide pin 1.1.3 laterally towards the end position PIII.

The guide pin 1.1.3 is firmly retained in the end position PIII, as the guide pin 1.1.3 abuts the U-shaped indent in the distal and in the lateral direction L. The flexible arm 1.1.4 is in the rest position, so that the guide pin 1.1.3 is laterally non-biased in the end position PIII. A lateral movement of the guide pin 1.1.3 is prevented by the form of the U-shaped indent of the guide track 1.2.5 at the end position PIII and by the flexible arm 1.1.4. Thus, the guide pin 1.1.3 in the end position PIII irreversibly locks the needle shield 1.1 into the advanced position III after a single use of the safety device 1.

In one embodiment of the invention, the hypodermic needle 2.1 is hidden from the view of the patient throughout the injection.

Figure 7:
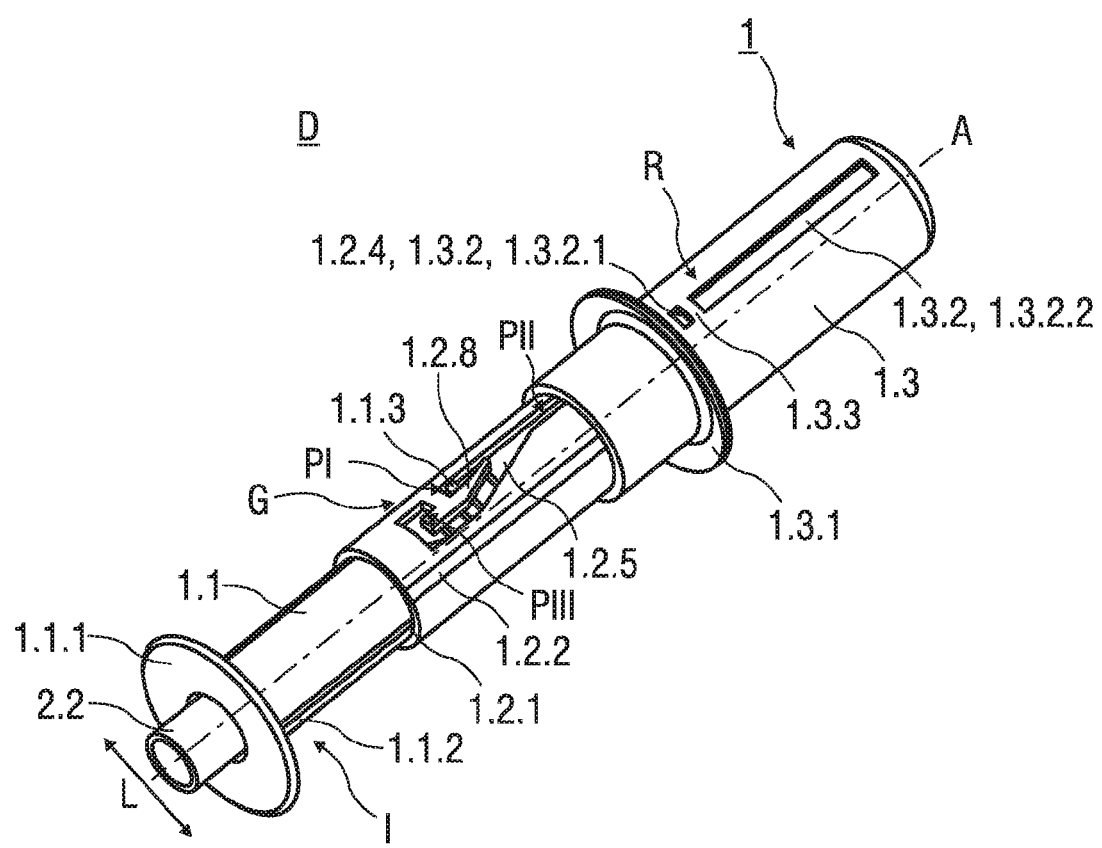
FIG. 7 shows a perspective view of an injection device according to a second embodiment of the invention.

FIG. 7 shows an injection device D according to a second embodiment of the invention, whereas, in comparison to the first embodiment, the guiding means G differ in shape and design. According to the second embodiment, the start position PI of the guide pin 1.1.3 is located between the distal and the proximal end of the guide track 1.2.5. The guide pin 1.1.3 in the start position PI retains the needle shield 1.1 in the initial position I. The guide pin 1.3.1 is releasably retained in the start position PI by a flexing gate element 1.2.8 that is laterally deflectable. When the needle shield 1.1 is pushed with respect to the support body 1.2 in the proximal direction during the first stage of the injection, the guide pin 1.1.3 leaves the start position PI towards an intermediate position PII located at the distal end of the guide track 1.2.5. Correspondingly, the needle shield 1.1 moves proximally from the initial position I to the retracted position II.

During the first stage of the injection, the telescoping movement of the outer body 1.3 with respect to the support body 1.2 is restricted and blocked by the retaining means R, wherein the radial projection 1.2.3 protrudes into the first section 1.3.2.1 of the longitudinal recess 1.3.2.

Upon reaching the retracted position II, the hypodermic needle 2.1 penetrates the skin of the patient. A force required to move the needle shield 1.1 further distally exceeds the retention force of the retaining means R. At the beginning of the second stage of the injection, the radial projection 1.2.3 overcomes the web 1.3.3 separating the first section 1.3.2.1 from the second section 1.3.2.2 of the longitudinal recess 1.3.2. As the second section 1.3.2.2 extends over a substantial axial length of the outer body 1.3, the radial projection 1.2.3 is allowed to move within the second section 1.3.2.2 of the longitudinal recess 1.3.2, so that the outer body 1.3 is allowed to move with respect to the support body 1.2 in the distal direction to expel the medicament through the hypodermic needle 2.1.

After the medicament has been delivered, the injection device D is removed from the injection site. The compression spring 1.4 arranged within the safety device 1 relaxes and moves the needle shield 1.1 towards the advanced position III. The guide pin 1.1.3 jointly moves with the needle shield 1.1 in the distal direction, whereby the flexing gate element 1.2.8 prevents the guide pin 1.1.3 from re-entering the start position PI and guides the guide pin 1.1.3 along the guide track 1.2.5 further in the distal direction. The guide pin finally enters the U-shaped indent defining the end position PIII that is located at the distal end of the guide track 1.2.5. The guide pin 1.1.3 is permanently retained in the end position PIII, so that the needle shield 1.1 is locked to the corresponding advanced position III after the first use of the injection device D.

The injection device D presented herein provides a simple mechanism to perform a stage-wise movement of the telescoping needle shield 1.1, support body 1.2 and outer body 1.3. The injection is carried out by orientating the central axis A of the safety device 1 essentially perpendicular to the skin surface of the patient and manually moving the outer body 1.3 towards the skin of the patient in a single linear stroke. In the first stage of the injection, the needle shield 1.1 is moved with respect to the support body 1.2 in a proximal direction. At the end of the first stage of the injection, the hypodermic needle 2.1 penetrates the skin of the patient. Subsequently, the retaining means R are released, so that the outer body 1.3 is allowed to move with respect to the support body 1.2 in the distal direction in the second stage of the injection, wherein the medicament is delivered beneath the skin of the patient.

Throughout the injection, the movement of the needle shield 1.1 relative to the support body 1.2 is controlled by the guiding means G comprising at least one guide track 1.2.5 and a guide pin 1.1.3. The interaction between the guide pin 1.1.3 and the guide track 1.2.5 is adapted to the retaining means R, so that the outer body 1.3 is allowed to move with respect to the support body 1.2 only after the hypodermic needle 2.1 has been inserted into the skin of the patient.

Figure 8:
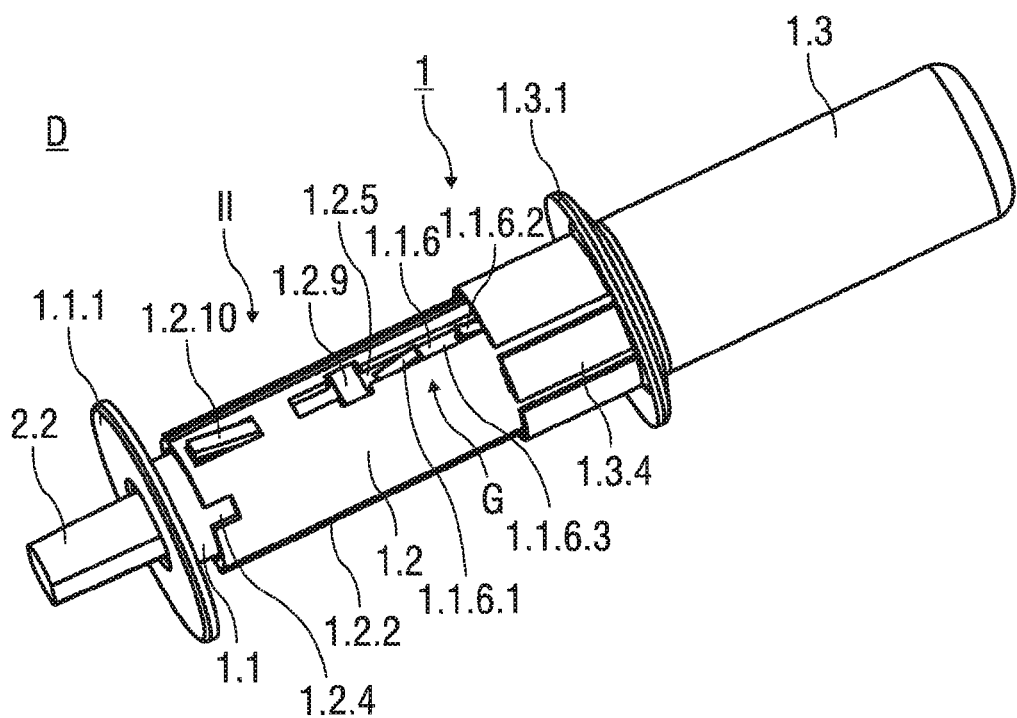
FIG. 8 shows a perspective view of an injection device according to a third embodiment of the invention.

FIG. 8 shows a third embodiment of the injection device D in a packaged state as it would be presented to a user. The guiding means G comprise two linear guide tracks 1.2.5 that are formed into opposite sides of the support body 1.2. The guide track 1.2.5 of the third embodiment is divided by a lateral separator 1.2.9 into two sections. The guide track 1.2.2 is adapted to accommodate a radial protrusion 1.1.6 that formed to an outer surface of the needle shield 1.1. The radial protrusion 1.1.6 comprises a distal ramp 1.1.6.1 and a proximal ramp 1.1.6.2. A notch 1.1.6.3 located the distal and the proximal ramp 1.1.6.1, 1.1.6.2 that is adapted to clip to the lateral separator 1.2.9 to lock the needle shield 1.1 into the advanced position III after an injection has been carried out.

A flap 1.2.10 is connected to the support body 1.2 via a hinge. The flap 1.2.10 projects radial outwardly from the support body 1.2 and is adapted to be engaged and pressed inwards when the outer body 1.3 receives the support body 1.1 at the end of an injection stroke.

The needle shield 1.1 of the injection device D according to the third embodiment is initially retained in the retracted position II. The needle cap 2.2 covering the hypodermic needle 2.1 projects distally from the needle shield 1.1 and may conveniently be removed prior the injection.

The outer body 1.3, the support body 1.2 and the needle shield 1.1 are telescopably arranged with respect to each other. As in the first and second embodiment, a relative rotation between the outer body 1.3 and the support body 1.2 is prevented by a second longitudinal tongue 1.2.2 that is received in a correspondingly shaped groove (not illustrated) formed into the inner surface of the outer body 1.3.

Figure 9:
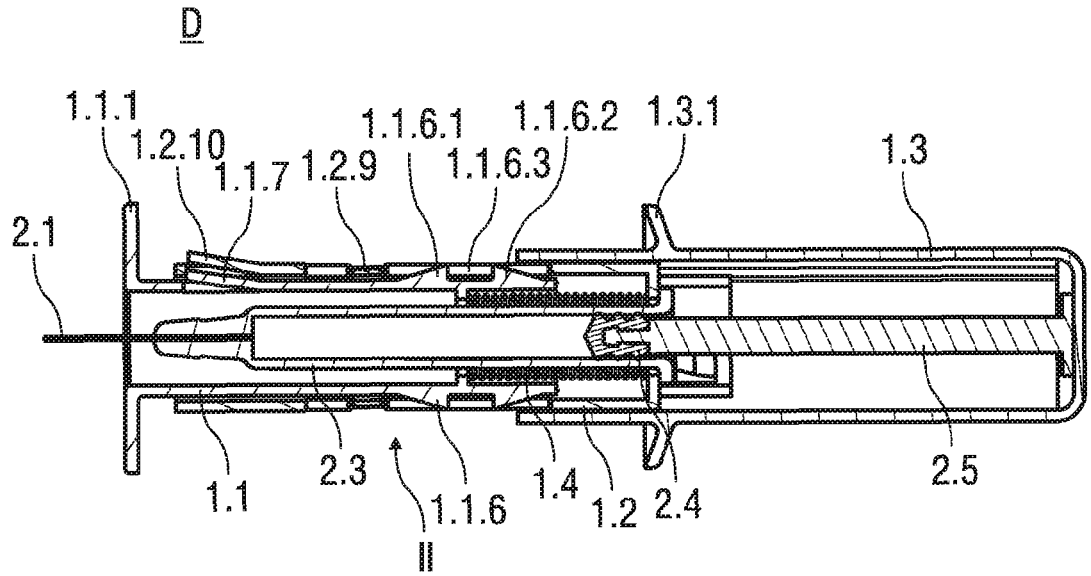
FIG. 9 shows a sectional view of the injection device according to the third embodiment with the needle shield initially retained in an retracted position.

FIG. 9 shows the injection device D according to the third embodiment in a sectional view. The needle shield 1.1 is releasably retained in the retracted position II by a detent 1.1.7 latching to the support body 1.2. The detent 1.1.7 abuts on the flap 1.2.10 and is inwardly deflectable, so that the needle shield 1.1 may be released from being retained in the retracted position II by pressing the flap 1.2.10 radial inwards.

With the needle shield 1.1 arranged in the refracted position II, the compression spring 1.4 bearing against inner surfaces of the needle shield 1.1 and the support body 1.2 is fully compressed and biases the needle shield towards the advanced position III. The radial protrusion 1.1.6 is located proximal of the lateral separator 1.2.9 and may slide, upon release of the needle shield 1.1, within the guide track 1.2.5 in the distal direction.

Figure 10:
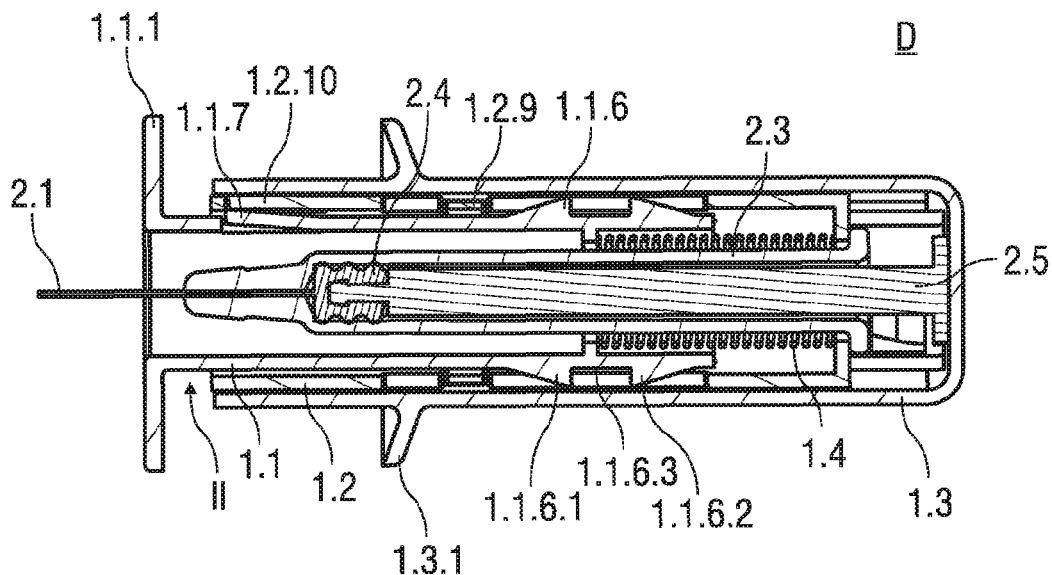
FIG. 10 shows a sectional view of the injection device according to the third embodiment at the end of an injection stroke.

FIG. 10 shows a sectional view of the injection device according to the third embodiment at the end of an injection stroke. The outer body 1.3 is slid over the support body 1.2 and the inner surface of the outer body 1.3 engages the flap 1.2.10. The flap 1.2.10 is pivots inwards and abuts against the detent 1.1.7 that is deflected radial inwards to disengage from and release the needle shield 1.1.

Figure 11:
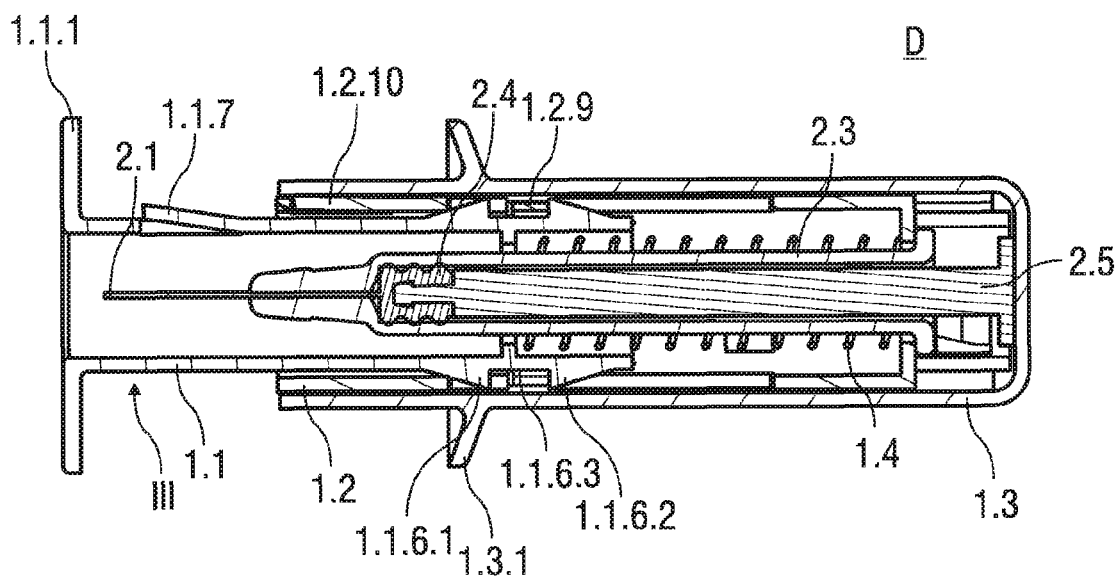
FIG. 11 shows a sectional view of the injection device according to the third embodiment with the needle shield located in an advanced position.

FIG. 11 shows a sectional view of the injection device according to the third embodiment after the injection in a needle shielding state. The needle shield 1.1 projects distally from the support body 1.2 in the advanced position III and covers the hypodermic needle 2.1 to prevent accidental needle stick injuries. The lateral separator 1.2.9 is firmly retained in the notch 1.1.6.3 of the radial protrusion 1.1.6 to permanently lock the needle shield 1.1 in the advanced position III preventing re-use of the injection device D in a second injection. The locking mechanism prevents a subsequent movement of the needle shield in both the distal and the proximal direction.

The operation mode of the injection device D according to the third embodiment is similar to the first and second embodiments described herein before. After removal of the needle cap 2.2, the hypodermic needle 2.2 is inserted into the skin of the patient receiving the injection. The skin-contact flange 1.1.1 of the needle shield 1.1 rests on the skin surface of the patient during the injection. The injection is carried out by simply manually pushing the outer body 1.3 towards the skin surface in a single linear injection stroke.

In a first stage, the outer body 1.3 is pushed distally to translate the piston 2.4 towards the distal end of the barrel 2.5, whereby the medicament contained in the pre-filled syringe 2 is disposed beneath the skin of the patient. At the end of the injection stroke indicated in FIG. 10, the inner surface of outer body 1.3 engages the flap 1.2.10. The flap 1.2.10 pivots inwardly and pushes the detent 1.1.7 out of engagement with the support body 1.3 releasing the retention of the needle shield 1.1 in the retracted position II.

In a second stage, the injection device D is removed from the skin of the patient. Upon removal, the compression spring 1.4 relaxes and moves towards the advanced position III shown in FIG. 11, whereby the radial protrusion 1.1.6 travels along the linear guide track 1.2.5 in the distal direction. The distal ramp 1.1.6.1 assists the projection 1.1.6 in overcoming the lateral separator 1.2.9 until the lateral separator 1.2.9 is retained within the notch 1.1.6.3 to irreversibly lock the needle shield 1.1 into the advanced position III preventing re-use of the injection device D.

Figure 12:
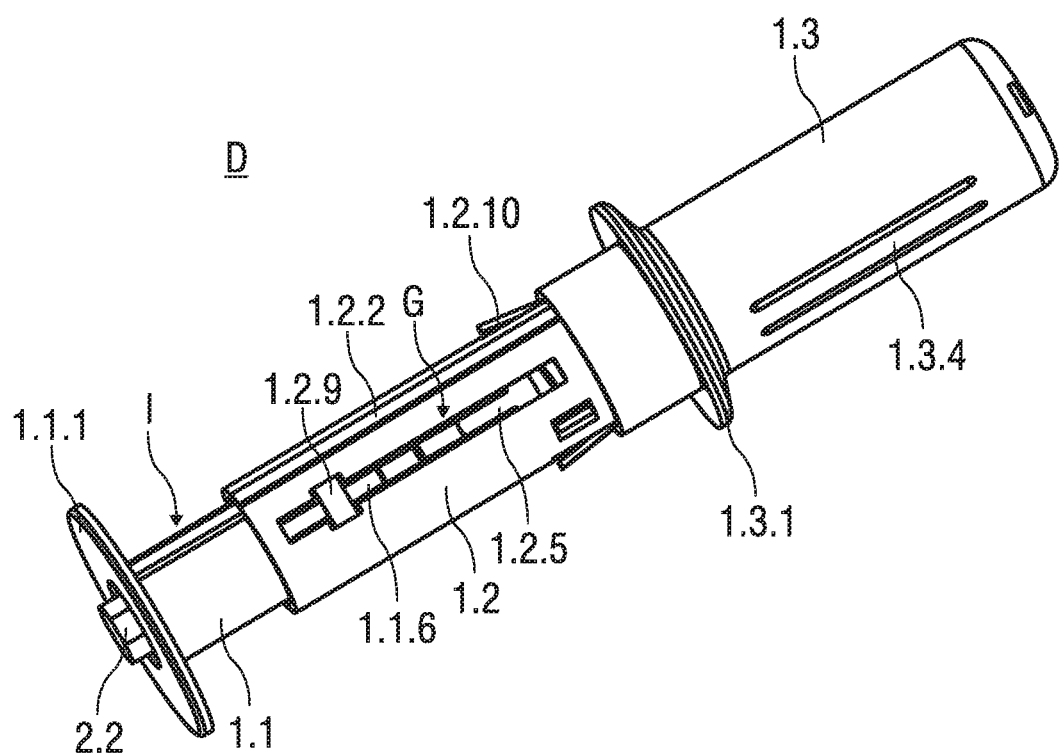
FIG. 12 shows a perspective view of an injection device according to a fourth embodiment of the invention.

FIG. 12 shows the injection device D according to a fourth embodiment of the invention in a perspective view. The guiding means G of the fourth embodiment is similar in design to the third embodiment. The radial protrusion 1.1.6 is slidably arranged within the linear guide track 1.2.5 and adapted to latch to the lateral separator 1.2.9 to provide a bi-directional locking means that prevents a re-exposure of the hypodermic needle 2.1 after completion of the injection.

Figure 13:
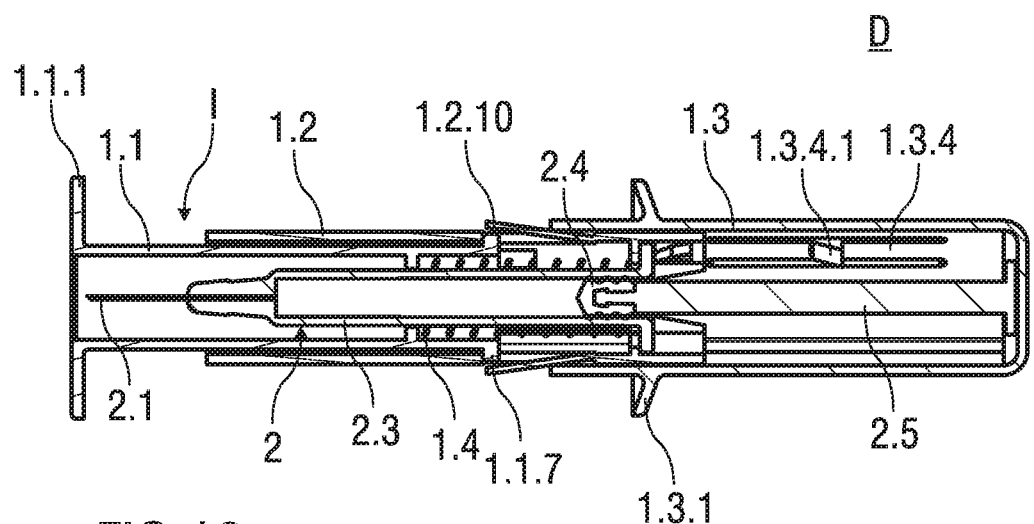
FIG. 13 shows a first sectional view of an injection device according to the fourth embodiment with the needle shield retained in the initial position.

FIG. 13 shows the injection device D of the fourth embodiment before the injection in first sectional view. The needle shield 1.1 is positioned in the initial state I. The flap 1.2.10 of the fourth embodiment is located in proximity of the proximal end of the support body 1.2. The flap 1.2.10 is arranged to release the detent 1.1.7 retaining the needle shield 1.1 in the initial position I.

The outer body 1.3 of the fourth embodiment comprises the clamp arm 1.3.4 with the inwardly protruding locking catch 1.3.4.1 that is adapted to latch to the support body 1.2 when the support body 1.2 is fully depressed into the outer body 1.3 at the end of the injection stroke.

Figure 14:
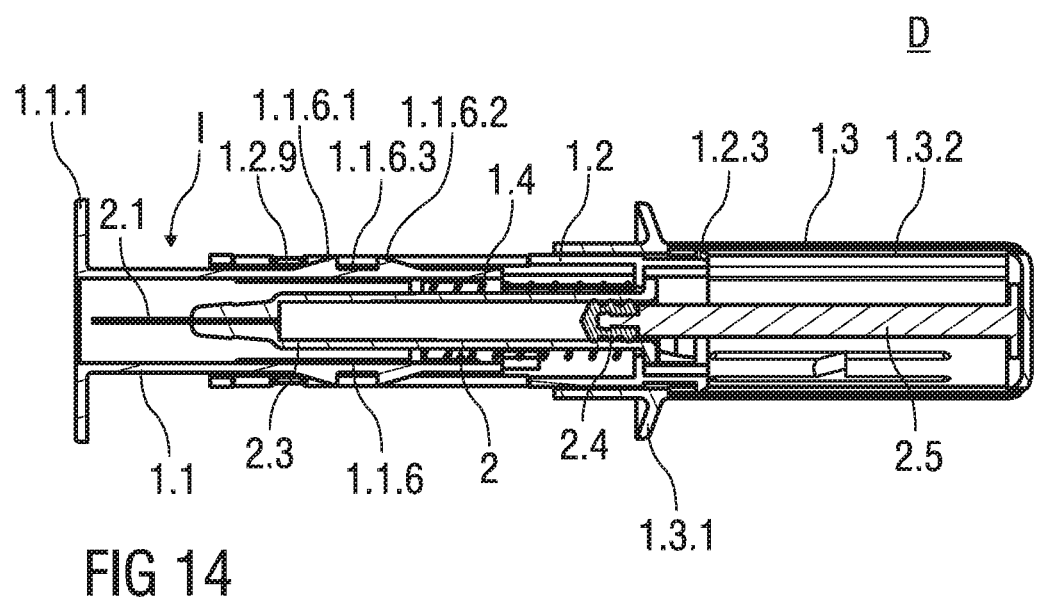
FIG. 14 shows a second sectional view of an injection device according to the fourth embodiment with the needle shield retained in the initial position.

FIG. 14 shows the injection device D of the fourth embodiment before the injection in second sectional view. The sectional plane shown in FIG. 14 extends substantially perpendicular to the one shown in FIG. 13 and shows the radial protrusion 1.1.6 retained disposed within the guide track 1.2.5. The outer body 1.3 further comprises the longitudinal recess 1.3.2 that accommodates the radial projection 1.2.3. The radial projection 1.2.3 travels along the longitudinal recess 1.3.2 formed into the inner surface of the outer body 1.3 when the outer body 1.3 is manually pushed in the distal direction to deliver the medicament contained in the pre-filled syringe 2 beneath the patient's skin. The engagement of the radial projection 1.2.3 and the longitudinal recess 1.3.2 prevents a relative rotation of the outer body 1.3 and the support body 1.2.

Additionally, the longitudinal recess 1.3.2 may comprise the web 1.3.3 that the radial projection 1.2.3 has to overcome before the outer body 1.3 is allowed to telescope with respect to the support body 1.2. The web 1.3.3 interacting with the radial projection 1.2.3 provides a retaining means R that prevents a movement of the outer body 1.3 until the needle shield 1.1 has reached the retracted position II and the hypodermic needle 2.1 is inserted into the skin of the patient. In particular, so-called wet injections, wherein the medicament contained in the pre-filled syringe 2 partially expelled before proper insertion of the hypodermic needle 2.1, are thus prevented.

Figure 15:
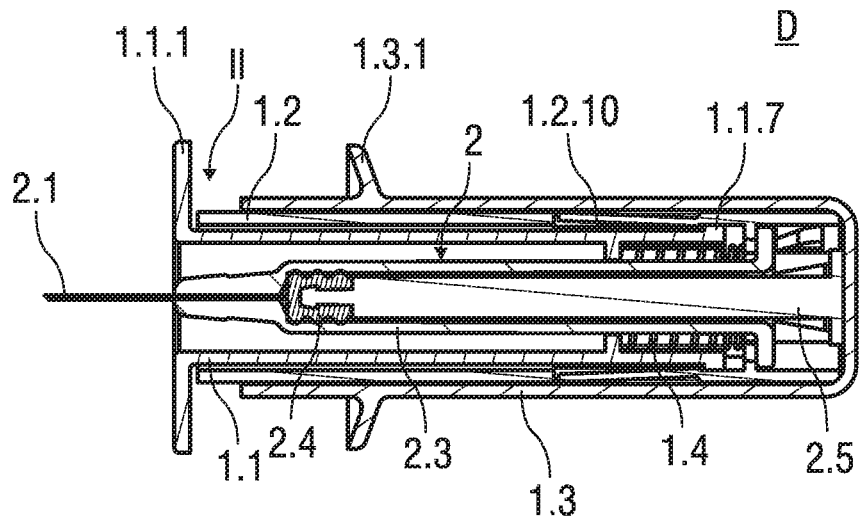
FIG. 15 shows a second sectional view of an injection device according to the fourth embodiment at the end of an injection stroke.

FIG. 15 shows a sectional view of the injection device D according to the fourth embodiment at the end of the drug delivery phase of the injection. The needle shield 1.1 is located in the retracted position II and the plunger 2.5 is fully depressed into the inner cavity 2.3.1 of the barrel 2.3. The support body 1.2 is depressed into the outer body 1.3 and the inner surface of the outer body 1.3 pushes the flap 1.2.10 radial inwards against the detent 1.1.7. The detent 1.1.7 deflected radial inwards to release the needle shield 1.1 from being retained in the retracted position II.

Figure 16:
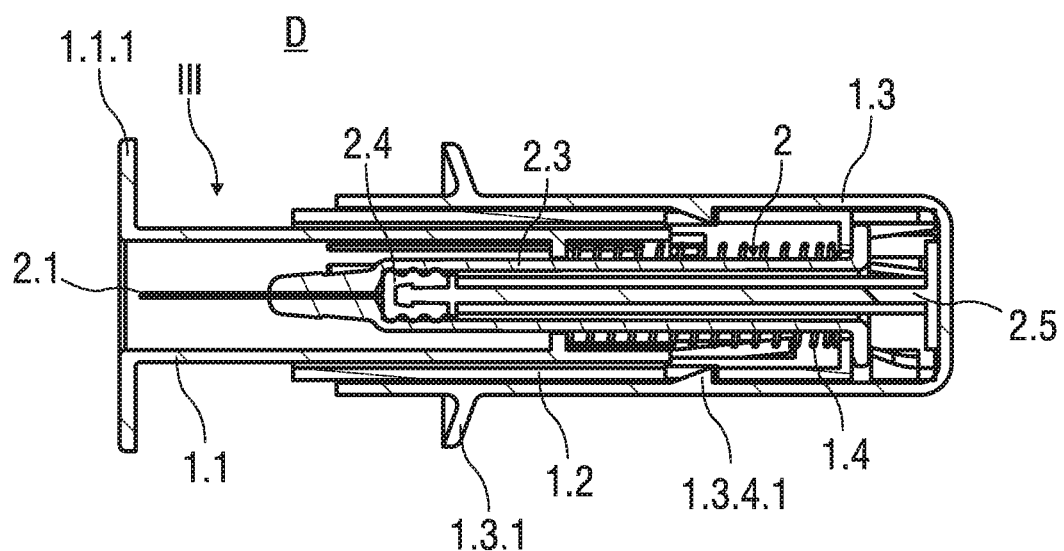
FIG. 16 shows a sectional view of the injection device according to the fourth embodiment with the needle shield located in the advanced position.

FIG. 16 shoes a sectional view of the injection device D according to the fourth embodiment after completion of the injection. The needle shield 1.1 is locked in the advanced position III covering the hypodermic needle 2.1. The locking catch 1.3.4.1 engages a corresponding notch formed into the support body 1.2 to permanently lock the outer body 1.3 to the support body 1.2. In this locked position, the guide track 1.2.5 retaining the radial protrusion 1.1.6 latching to the lateral separator 1.2.9 to lock the needle shield 1.1 in the advanced position II is covered by the outer body 1.3. This in particular prevents the user from tampering with the guiding means G locking the needle shield into the forward advanced position III. Thus, the injection device D cannot be altered to be used in a second injection which reduces the risk of the transmission of infectious diseases caused by needle stick injuries with contaminated needles.

The injection device D according to the fourth embodiment is essentially used during an injection as described herein before. In particular, the injection may be performed in stages: the outer body 1.3 is essentially restricted from moving distally until the hypodermic needle 2.1 is inserted into the skin of the patient avoiding a spilling of the medicament. Only after completion of the injection phase delivering the medicament beneath the skin of the patient and upon removal of the injection device D from the injection site, the compression spring 1.4 may drive the needle shield 1.1 into the advanced position III shielding the hypodermic needle 2.1. The guiding means G guide the movement of the needle shield 1.1 relative to the support body 1.2. The guiding means G of the fourth embodiment are designed and work as the one of the third embodiment described herein before and in particular provide a bi-directional lock that inhibits the needle shield 1.1 in the advanced position III from moving in the distal and in the proximal direction.

Unless explicitly stated otherwise, different features disclosed in the different embodiments described herein before may advantageously combined. For example, the fourth embodiment may additionally comprise the retaining means R inhibiting the proximal movement of the outer body 1.3 until the needle shield 1.1 reaches the retracted position II. However, other suitable combinations of various features of the different embodiments described herein are possible and within the scope of the present invention.

The invention claimed is:

1. An injection device comprising
    a syringe pre-filled with medicament comprising,
        a barrel;
        a needle having a distal end and a proximal end, the proximal end attached to a distal end of the syringe; and
        a sliding piston sealing a proximal end of the barrel, where the syringe is contained within an assembly comprising a support body, a needle shield and an outer body, where the assembly is configured to transform from a first stage to a second stage to a third stage during a process where the medicament is expelled from the barrel of the syringe through the needle, where the outer body, is operably connected to the piston;

is rotatably fixed relative to the support body; and is configured to engage a flap on the support body when the assembly transforms from the first stage to the second stage causing the flap to engage and unlatch a detent on the needle shield, where the needle shield, has a distal opening that is axially positioned relative to the distal end of the needle such the distal end of the needle protrudes outwardly of the distal opening exposing the needle when the assembly is in the first stage and in the second stage, where the distal opening covers the distal end of the needle when the assembly is in the third stage;

is biased in a distal direction such that the needle shield telescopably extends relative to the support body as the assembly transforms from the second stage to the third stage; and is permanently locked axially in an extended positioned through engagement of a radial protrusion on the needle shield with a lateral separator located in a guide track on the support body when the assembly is in the third stage.

2. An injection device according to claim 1, where a piston rod connected to the piston abuts the outer body or is integral with the outer body as one piece.

3. An injection device according to claim 1, where the radial protrusion contains a notch that engages and permanently retains the lateral separator when the assembly is in the third stage.

4. An injection device according to claim 1, where the needle shield is releasably retained in a retracted position by the detent being flexibly engaged with a distal end of the support body when the assembly is in the first stage.

5. An injection device according to claim 1, where the needle shield is biased in a distal direction by a spring engaged on one end with the needle shield and on another end with the support body.

6. An injection device according to claim 1, where the distal opening is configured with a skin-contact flange.

7. An injection device according to claim 1, where the flap is pressed radially inwardly by an inside distal end of the outer body as the assembly is transformed to the second stage.

8. An injection device according to claim 7, where the radially inward movement of the flap simultaneously causes inward radial flexing of the detent disengaging the detent from a retained positioned with the support body.

9. An injection device according to claim 5 where the spring is a compression spring and is in a compressed state when the assembly is in the first and second stages and is in a relaxed state when the assembly is in the third stage.

10. An injection device according to claim 1, where the radial protrusion is located proximal of the lateral separator when the assembly is in the second stage and slides within the guide track as the assembly transforms from the second stage to the third stage.

11. An injection device according to claim 1, where the outer body is telescopably arranged with and is rotatably fixed relative to the support body through engagement of a longitudinal tongue with an inner surface of the outer body.

* * * * *